US010500149B2

(12) United States Patent
Lago et al.

(10) Patent No.: US 10,500,149 B2
(45) Date of Patent: Dec. 10, 2019

(54) AQUEOUS COLORANT COMPOSITION AND USE THEREOF

(71) Applicants: Natura Cosméticos S.A., São Paulo (BR); Warner Babcock Institute for Green Chemistry, LLC, Wilmington, MA (US)

(72) Inventors: Juliana Carvalhäes Lago, São Paulo (BR); Adriana de Andrade Fregonesi, São Paulo (BR); Ana Paula Pedroso De Oliveira, São Paulo (BR); John C. Warner, Wilmington, MA (US); Laura Muollo, Dracut, MA (US); Jennifer Cookson, Arlington, MA (US); Carla Scanavez, São Paulo (BR)

(73) Assignees: NATURAL COSMETICOS S.A., Sao Paulo (BR); WARNER BABCOCK INSTITUTE FOR GREEN CHEMISTRY, LLC, Wilmington, MA (US)

( * ) Notice: Subject to any disclaimer, the term of this patent is extended or adjusted under 35 U.S.C. 154(b) by 0 days.

(21) Appl. No.: 14/984,930

(22) Filed: Dec. 30, 2015

(65) Prior Publication Data
US 2017/0189310 A1 Jul. 6, 2017

(51) Int. Cl.
A61Q 5/10 (2006.01)
A61K 8/85 (2006.01)
A61K 8/24 (2006.01)
A61Q 5/06 (2006.01)

(52) U.S. Cl.
CPC .......... *A61K 8/85* (2013.01); *A61K 8/24* (2013.01); *A61Q 5/065* (2013.01); *A61Q 5/10* (2013.01); *A61K 2800/432* (2013.01); *A61K 2800/884* (2013.01)

(58) Field of Classification Search
CPC ...... A61Q 5/10; A61K 8/85; A61K 2800/432; A61K 2800/884
See application file for complete search history.

(56) References Cited

U.S. PATENT DOCUMENTS

| | | | |
|---|---|---|---|
| 2002/0034486 A1* | 3/2002 | Midha | A61K 8/0245 424/70.2 |
| 2008/0104773 A1* | 5/2008 | Weser | A61K 8/645 8/409 |
| 2014/0199256 A1 | 7/2014 | Sasik et al. | |
| 2014/0290689 A1* | 10/2014 | Sutton | A61Q 5/065 132/208 |

FOREIGN PATENT DOCUMENTS

WO  WO 2006086444  8/2006

OTHER PUBLICATIONS

"Liquid Foundation SPF" [online][retrieved online Oct. 21, 2019], retrieved from the Internet; <http://www.gnpd.com> dated (Mar. 2015).
Extended European Search Report for Application No. 16880211.4 dated Sep. 12, 2019.

* cited by examiner

*Primary Examiner* — Eisa B Elhilo
(74) *Attorney, Agent, or Firm* — Alston & Bird LLP

(57) ABSTRACT

The present invention refers to an aqueous colorant composition comprising poly(lactic acid) (PLA) and a colorant. The invention also refers to the uses of said composition particularly in methods for coloring hair.

8 Claims, 1 Drawing Sheet

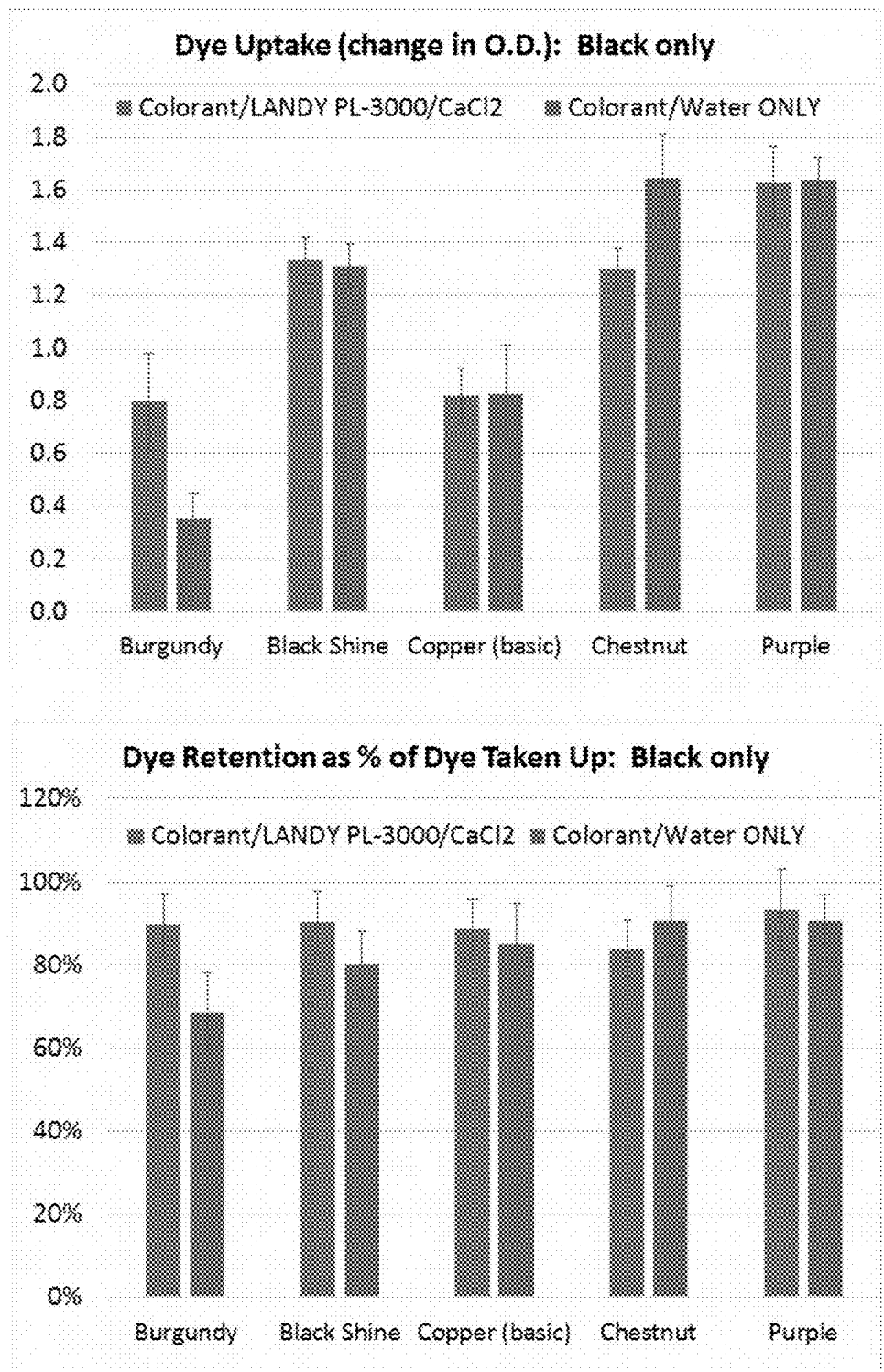

AQUEOUS COLORANT COMPOSITION AND USE THEREOF

TECHNICAL FIELD

Described herein are aqueous polymer-containing colorant compositions useful in hair coloring and other uses. More particularly, described herein are methods and compositions useful for enhancing uptake and retention of dye on hair strands.

BACKGROUND

Most permanent hair coloring products contain a pigment, developer and an alkalizing agent. The developer is usually an oxidizing agent such as hydrogen peroxide in water or a cream lotion. The alkalizing agent is most often ammonia or an ammonia substitute that causes the hair to swell.

Chemicals found in synthetic hair dyes, including ammonia, lead, and/or coal tar, are toxic and can have dangerous side-effects such as hair loss, burning, redness, itchy skin, swelling, or trouble breathing. Many people forego hair coloring to avoid exposure to the chemicals found in the coloring compositions.

Hair colorants that are classified as "direct dyes" do not require further chemical modification in the coloring process. In contrast to "oxidation dyes", which color hair by oxidation of a dye precursor during the coloring process, direct dyes do not require a chemical oxidant in the coloring composition. For example, acid dyes are direct dyes that accomplish hair coloring by forming an ionic bond between the dye and a positively-charged amino acid residue within the hair shaft. However, this ionic bond is typically cleaved when hair is shampooed, resulting in the dye being released from the hair.

Because direct dyes are generally not retained in or on the hair shaft (and, if used as hair colorants, are readily washed out of the hair), mechanisms which enhance direct dye uptake and retention are needed. If a chemical such as ammonia is used to swell the hair cuticle, direct dye penetration and retention in the hair shaft is still quite low.

A chemical fixative (such as a metal-containing mordanting agent) can increase retention of a direct dye on hair strands. However, traditional compositions containing a fixative may cause sensitization or allergic reactions in some individuals. Fixatives and corresponding hair coloring methods also often contain heavy metal or aluminum ions, some of which have been linked to neurological and other disorders. Some fixative formulations contain siloxanes which) can be toxic, persistent, and bio-accumulative. Most also contain organic solvents, which present flammability hazards and can have an undesirable drying effect on the hair.

There is a current need for a benign and effective method of enhancing dye uptake and retention on hair, which avoids the use of chemical oxidants, fixatives, mordanting agents, bleaching or swelling agents, and other substances that may cause undesired health effects.

SUMMARY

Described herein are colorant compositions and methods of using them that are bio-based, aqueous formulations that avoid the use of chemical oxidants, fixatives, mordanting agents, bleaching or swelling agents or other substances that may cause undesired health effects.

Accordingly, described herein is an aqueous colorant composition comprising poly(lactic acid) (PLA) and a colorant.

Also described herein is a method of coloring hair comprising the step of applying to the hair an aqueous colorant composition comprising PLA and a colorant. Another method of coloring hair is described comprising the steps of first applying to the hair an aqueous PLA dispersion; and then subsequently applying a colorant to the hair.

The following embodiments, aspects and variations thereof are exemplary and illustrative, and are not intended to be limiting in scope.

BRIEF DESCRIPTION OF THE FIGURES

The sole FIGURE shows dye uptake and retention for coloring compositions with and without poly(lactic acid) (PLA).

DETAILED DESCRIPTION

Definitions

Unless specifically noted otherwise herein, the definitions of the terms used are standard definitions used in the art of hair coloring and chemistry science. Exemplary embodiments, aspects and variations are illustrative in the figures and drawings, and it is intended that the embodiments, aspects and variations, and the figures and drawings disclosed herein are to be considered illustrative and not limiting.

As used herein the term "colorant" refers to dyes, pigments and combinations thereof, and the term coloring is intended to mean dyeing, pigmenting and combinations thereof.

Hair Colorant Compositions

Described herein are hair colorant compositions that are aqueous formulations that avoid the use of chemical oxidants, fixatives, mordanting agents, bleaching or swelling agents or other substances that may cause undesired health effects.

The compositions described herein comprise an aqueous solution of poly(lactic acid) and a colorant. Preferably the poly(lactic acid) is provided as an aqueous dispersion, and the colorant is a direct dye.

The poly(lactic acid) (PLA) described herein comprises 0.1 to 85 wt %, preferably 1 to 50 wt %, preferably 2.5 to 15 wt %, and more preferably 5.8-6.0 wt %. of the total colorant composition. PLA may be conveniently supplied as a commercial dispersion such as LANDY PL-3000® (Miyoshi Oil & Fat Co. Ltd., Aichi, Japan), or as a white powder such as PL POWDER (Miyoshi Oil & Fat Co. Ltd., Aichi, Japan) or Asensa NCL 111 (Honeywell International, Morristown, N.J.). LANDY PL-3000 is comprised of 29.4% (w/w) PLA in water. In a preferred colorant composition comprised of 20% LANDY PL-3000, that composition therefore contains 5.9% PLA by weight.

The colorant described herein is preferably a "direct dye" (one that requires no chemical alteration during the coloring process), and may optionally be a mix of one or more direct dyes. Direct dyes are well known in the art and may be acidic, basic or neutral. Some typical direct dyes include, but are not limited to, Acid Red 14, Acid Red 18, Acid Red 33, Acid Red 52, Acid Red 87 Acid Yellow 3, Acid Yellow 23, Acid Orange 7, Acid Violet 43, Acid Blue 9, Acid Green 25, Acid Black 1, Basic Brown 16, Basic Brown 17, Basic Red 51, Basic Red 76, Basic Yellow 57, and Basic Blue 99. Other direct dyes approved by the U.S. Food and Drug Administration are listed in its "Color Additives Permitted for Use in Cosmetics."

There is no single preferred colorant amount in the compositions of the invention. A colorant that acts as a whitener or tinting agent may comprise only 0.01% or less of the colorant composition. Other colorants will typically comprise 0.1 to 5 wt % or more of the colorant composition.

The colorant composition described herein may also contain a salt of a metal ion. The salt is preferably a soluble salt, and preferably a soluble calcium salt such as calcium chloride ($CaCl_2$). The final colorant composition, if it contains a metal salt, is generally 0.01 to 5 wt % salt, more preferably 0.1 to 1.0 wt % salt, and most preferably 0.25 wt % salt. Other suitable salts include sodium chloride (NaCl), potassium chloride (KCl), magnesium chloride ($MgCl_2$), manganese (II) chloride ($MnCl_2$), calcium lactate and hydrates thereof. Other suitable salts include soluble chlorides, lactates, gluconates, citrates and sulfates of sodium ($Na^+$), potassium ($K^+$), magnesium ($Mg^{2+}$), zinc ($Zn^{2+}$), copper ($Cu^+$ or $Cu^{2+}$) or iron ($Fe^{2+}$ or $Fe^{3+}$) and hydrates thereof.

The colorant composition described herein may also contain a mineral additive. The mineral additive is selected from the group consisting of clays (such as montmorillonite), diatomaceous earth, and hydroxyapatite. Preferably, the mineral additive is hydroxyapatite. The final colorant composition, if it contains a mineral additive, may be 0.01 to 5 wt % mineral additive, more preferably 0.5 to 1.5 wt % mineral additive, and most preferably 1 wt % mineral additive.

Method of Coloring Hair Using the Aqueous Colorant Composition

The colorant composition is typically applied to hair in a one-step procedure, in which the color is set by heating hair that has been coated with the composition for 5 to 60 min. The time and heating temperature may be adjusted so as to obtain the desired depth of color on the hair. Heating temperature is generally between 20-100° C. Most typically: first, the colorant composition is applied to hair, then the coated hair is enclosed in aluminum foil packets, and then the colorant composition-coated, foil-wrapped hair is dried under a hooded hair dryer set to 'HI' (approximately 33-37° C.) for 30 min.

Hair coloring may also be achieved by an optional two-step procedure. In the first step, a poly(lactic acid) dispersion is applied to the hair, then, an aqueous composition of the direct dye colorant is applied to the hair. The one-step application procedure is preferred only in that it provides for a simpler and less time-consuming procedure for coloring hair.

The claimed invention does not use a chemical oxidant, fixative, mordanting agent, bleaching or swelling agent or other substance that may cause undesired health effects.

EXPERIMENTAL

Example 1

Effect of Polylactic Acid and Hydroxyapatite on Hair Coloring 20 hair colorant compositions were prepared as shown in Table 1. For preparations 1-7, solutions were prepared by combining 0.200 g colorant or colorants with 19.8 mL deionized water. The mixture was stirred until all of the direct dye colorant had dissolved. For preparations 8-14, 0.200 g of solid colorant dye and 2.00 g of LANDY PL-3000 were added to 17.8 mL of deionized water. The mixture was stirred with a stir bar until it appeared homogenous and all of the direct dye colorant had dissolved. And for preparations 15-20, 1.0 wt % hydroxyapatite (HA), 10.0 wt % LANDY PL-3000, and a given wt % of colorant or colorants were added to a volume of deionized water. The dispersion was mixed with a stir bar until it appeared homogenous and all of the direct dye colorant had dissolved.

Hair samples were prepared by taking a bundle of hair strands approximately 5-6 cm long and of similar strand quantity, anywhere from about ½ to 1 gram each, and securing the strands together at one end with rubber cement.

Five dry, secured hair samples were placed on a sheet of aluminum foil, and then 1.5 mL of a given coloring composition per sample was dispensed onto hair samples. The dye mixture was worked into the hair samples using a standard salon color brush for 10-30 seconds, to ensure complete coverage of the samples. Samples were then transferred onto a clean sheet of aluminum foil, and a hand-held blow dryer used for approximately 15 minutes to dry the colorant dispersions onto the samples. Samples were then placed under a hooded Highland Venus+ hair dryer set to LOW heat, until all other samples in the set were prepared and dry.

A pea-sized amount (approx. 0.25 mL) of baby shampoo was placed onto each hair sample, and worked into a foam for approximately 10 seconds. Samples were then rinsed for approximately 30 seconds under tepid running tap water. One sample was then removed, and the excess water in that one sample squeezed out with a gloved forefinger and thumb. The sample was set aside and the remaining four samples washed a second time using the same method, with another sample being removed after washing and rinsing. The procedure was repeated so that the five samples comprise a set in which one sample was washed once, one sample washed twice, one sample washed three times, one sample washed four times, and one sample washed five times. After all washes and rinses were completed, all hair samples were then dried using a hand-held blow dryer set on HIGH.

In some instances, a total of six secured hair samples were colored, and the washing procedure was repeated so that the six samples comprise a set in which one sample was washed once, one sample washed twice, one sample washed three times, one sample washed four times, one sample washed five times, and one sample washed ten times.

Colorant uptake following the coloring procedure and colorant retention following washes was assessed visually. In each case, dye uptake and retention was increased for hair samples colored with PLA-colorant formulations compared to colorant-only preparations.

TABLE 1

Preparation and Coloring compositions of Preparations 1-20.
Balance of each composition is deionized water.

| Preparation Number | Colorant | wt % Colorant(s) | wt % LANDY PL-3000 | wt % HA |
|---|---|---|---|---|
| 1 | Acid Red 33 | 1.0 | — | — |
| 2 | Acid Yellow 23 | 1.0 | — | — |
| 3 | Acid Blue 9 | 1.0 | — | — |
| 4 | Acid Green 25 | 1.0 | — | — |
| 5 | Acid Black 1 | 0.5 | — | — |
| 6 | Basic Brown 16 | 1.0 | — | — |
| 7 | 5:1 Acid Yellow 23:Acid Red 33 | 0.17% Acid Yellow 23 0.83% Acid Red 33 | — | — |
| 8 | Acid Red 33 | 1.0 | 10.0 | — |
| 9 | Acid Yellow 23 | 1.0 | 10.0 | — |
| 10 | Acid Blue 9 | 1.0 | 10.0 | — |
| 11 | Acid Green 25 | 1.0 | 10.0 | — |
| 12 | Acid Black 1 | 0.5 | 10.0 | — |
| 13 | Basic Brown 16 | 1.0 | 10.0 | — |
| 14 | 5:1 Acid Yellow 23:Acid Red 33 | 0.17% Acid Yellow 23 0.83% Acid Red 33 | 10.0 | — |
| 15 | Acid Red 33 | 1.0 | 10.0 | 1.0 |
| 16 | Acid Yellow 23 | 1.0 | 10.0 | 1.0 |
| 17 | Acid Blue 9 | 1.0 | 10.0 | 1.0 |
| 18 | Acid Green 25 | 1.0 | 10.0 | 1.0 |
| 19 | Basic Brown 16 | 1.0 | 10.0 | 1.0 |
| 20 | 5:1 Acid Yellow 23:Acid Red 33 | 0.17% Acid Yellow 23 0.83% Acid Red 33 | 10.0 | 1.0 |

Example 2

Effect of Drying Temperature on Hair Coloring

Eight hair colorant compositions were prepared as shown in Table 2. For preparations 21-24, solutions were made by combining 0.200 g of Acid Green 25 with 19.8 mL of deionized water, and stirring the mixture until all dye dissolved. For preparations 25-28, dye mixtures were made by mixing 0.200 g of Acid Green 25, 2.00 g of LANDY PL-3000, and 17.8 mL of deionized water, and stirring the mixture until all dye dissolved and the mixture formed a uniform dispersion. Bleached hair samples were prepared and secured at one end as given in the methods of Example 1.

After each coloring composition was applied to the hair samples with a color brush, the samples were removed from the dye mixture, briefly drained, and each still-wet sample individually wrapped in aluminum foil. The wrapped samples were then placed under a hooded hair dryer. The hair dryer was set on LOW, MED, HI, or PERM heat setting. After 15 minutes, the temperature of the hair sample packets was determined using an infrared thermometer. Sample packets were then turned over and then dried for an additional 15 minutes at the same dryer setting. Sample packets were then removed from the dryer, and the samples removed from the foil and rinsed with tepid tap water. All samples were then dried using a hand-held blow dryer set on high temperature and high blower speed.

All samples were washed with baby shampoo, similar to the methods of Example 1. The five samples for each composition and temperature comprise a set in which one sample was washed once, one sample washed twice, one sample washed three times, one sample washed four times, and one sample washed five times.

Colorant uptake following the coloring procedure and colorant retention following washes was assessed visually. Preparation numbers, coloring compositions, and color setting parameters are given in Table 2. Dye uptake was the greatest for hair samples colored with PLA-colorant formulations comprised of LANDY PL-3000 and for which the color was set at 33-37° C. temperature at the samples using the HI dryer setting, as evidenced by darker coloration after coloring and following the first wash. Color retention was also greatest for samples colored with PLA-colorant formulations and the color set using the 'HI' dryer setting, as evidenced by darker coloration after five consecutive shampoo washes.

TABLE 2

Preparation, color compositions, and drying parameters for Preparations 21-28. Balance of each composition is deionized water.

| Preparation Number | Colorant | wt % Colorant(s) | wt % LANDY PL-3000 | Dryer Setting | Sample Temperatures |
|---|---|---|---|---|---|
| 21 | Acid Green 25 | 1.0 | — | LOW | 21-26° C. |
| 22 | Acid Green 25 | 1.0 | — | MED | 27-32° C. |
| 23 | Acid Green 25 | 1.0 | — | HI | 33-37° C. |
| 24 | Acid Green 25 | 1.0 | — | PERM | 38-43° C. |
| 25 | Acid Green 25 | 1.0 | 10.0 | LOW | 21-26° C. |
| 26 | Acid Green 25 | 1.0 | 10.0 | MED | 27-32° C. |

TABLE 2-continued

Preparation, color compositions, and drying parameters for
Preparations 21-28. Balance of each composition is deionized water.

| Preparation Number | Colorant | wt % Colorant(s) | wt % LANDY PL-3000 | Dryer Setting | Sample Temperatures |
|---|---|---|---|---|---|
| 27 | Acid Green 25 | 1.0 | 10.0 | HI | 33-37° C. |
| 28 | Acid Green 25 | 1.0 | 10.0 | PERM | 38-43° C. |

Example 3

Effect of Polylactic Acid Concentration on Hair Coloring 24 hair colorant compositions were prepared as shown in Table 4. For preparations 29-34, a 1% dye solution (control) was made by combining 0.200 g of Acid Green 25 with 19.8 mL of deionized water, and stirring the mixture until all dye dissolved. For preparations 35-52, a PLA-1% dye mixture was made by mixing 0.200 g of Acid Green 25, an appropriate weight of LANDY PL-3000, and a volume of deionized water to make up a total of 20.0 g of mixture, and stirring the mixture until all dye dissolved and the mixture formed a uniform dispersion. LANDY PL-3000 was added in amounts so as to comprise 10%, 20%, or 50% of the final composition. Bleached hair samples were prepared and secured at one end as given in the methods of Example 1.

After application of the coloring compositions to the hair samples with a color brush, the samples were removed from the dye mixture, briefly drained, and each still-wet sample individually wrapped in aluminum foil. The wrapped samples were then placed under a hooded Venus+ Hair Dryer set on HI. Sample packets were dried for a given number of minutes, after which two sample packets for each composition and time were removed from the dryer. The samples were then removed from the foil and rinsed with tepid tap water, then dried using a hand-held blow dryer set on high temperature and high blower speed.

After all samples had been removed from the hooded dryer, rinsed and dried, one hair sample for each Preparation, corresponding to a particular time and composition, was washed a total of five times with baby shampoo, similarly to the methods of Example 1.

Colorant uptake following the coloring procedure and colorant retention following washes was assessed visually. Preparation numbers, coloring compositions, and drying times are given in Table 3. For samples prepared with the same color setting time, higher PLA content in the coloring composition resulted in higher dye uptake and retention on multiple washes. For samples prepared with the same coloring composition, longer heat-set time resulted in greater dye uptake and the dye retention on multiple washes.

The darkest color was observed on hair samples colored using Preparations 51 and 52, in which the coloring composition was comprised of 50% LANDY PL-3000, and with the color set by 45 or 60 min under the hooded hair dryer. Little difference in dye uptake or retention was observed between the two preparations. Differences in samples that were not washed and those subjected to 5 washings, or between washed samples that were colored with compositions of differing PLA concentrations, is most visibly evident for samples with little dye uptake, because the human eye is more sensitive to slight shade differences at low amounts of color.

TABLE 3

Preparation, coloring compositions, and drying time of Preparations
29-52. Balance of each composition is deionized water.

| Preparation Number | Colorant | wt % Colorant(s) | wt % LANDY PL-3000 | Drying Time |
|---|---|---|---|---|
| 29 | Acid Green 25 | 1.0 | — | 5 min |
| 30 | Acid Green 25 | 1.0 | — | 10 min |
| 31 | Acid Green 25 | 1.0 | — | 20 min |
| 32 | Acid Green 25 | 1.0 | — | 30 min |
| 33 | Acid Green 25 | 1.0 | — | 45 min |
| 34 | Acid Green 25 | 1.0 | — | 60 min |
| 35 | Acid Green 25 | 1.0 | 10.0 | 5 min |
| 36 | Acid Green 25 | 1.0 | 10.0 | 10 min |
| 37 | Acid Green 25 | 1.0 | 10.0 | 20 mm |
| 38 | Acid Green 25 | 1.0 | 10.0 | 30 min |
| 39 | Acid Green 25 | 1.0 | 10.0 | 45 min |
| 40 | Acid Green 25 | 1.0 | 10.0 | 60 min |
| 41 | Acid Green 25 | 1.0 | 20.0 | 5 min |
| 42 | Acid Green 25 | 1.0 | 20.0 | 10 min |
| 43 | Acid Green 25 | 1.0 | 20.0 | 20 min |
| 44 | Acid Green 25 | 1.0 | 20.0 | 30 min |
| 45 | Acid Green 25 | 1.0 | 20.0 | 45 min |
| 46 | Acid Green 25 | 1.0 | 20.0 | 60 min |
| 47 | Acid Green 25 | 1.0 | 50.0 | 5 min |
| 48 | Acid Green 25 | 1.0 | 50.0 | 10 min |
| 49 | Acid Green 25 | 1.0 | 50.0 | 20 min |
| 50 | Acid Green 25 | 1.0 | 50.0 | 30 min |
| 51 | Acid Green 25 | 1.0 | 50.0 | 45 min |
| 52 | Acid Green 25 | 1.0 | 50.0 | 60 min |

Example 4

One-step and Two-step Processes

Mixtures A, B, C, D, and E were prepared according to the compositions of Table 4 by mixing all components until a homogeneous dispersion was formed and all colorant, if used, was completely dissolved.

TABLE 4

Compositions of Mixtures A-E.

| Mixture | Mixture Components | total volume (mL) | Acid Green 25 (g) | LANDY PL-3000 (g) | water (mL) |
|---|---|---|---|---|---|
| A | Acid Green 25 (1.0%) LANDY PL-3000 (20%) | 10 mL | 0.010 g | 2.0 g | 7.99 |
| B | Acid Green 25 (0.1%) LANDY PL-3000 (20%) | 10 mL | 0.100 g | 2.0 g | 7.90 |
| C | LANDY PL-3000 (20%) | 20 mL | none | 4.0 g | 16.00 |
| D | Acid Green 25 (1.0% aq.) | 10 mL | 0.010 g | none | 9.99 |
| E | Acid Green 25 (0.1% aq.) | 10 mL | 0.100 g | none | 9.90 |

Sixteen bleached hair samples, consisting of two samples for each of Preparations 53-60, as given in Color uptake was increased for any of the 1-step or 2-step procedures when 1.0% colorant is used as compared to 0.1% colorant. Dye retention was more difficult to assess visually.

The 2-step application method in which the hair is first treated with a PLA dispersion followed by treatment with colorant solution results in comparable uptake and comparable color retention following multiple shampooing as compared to the one-step (simultaneous) application of colorant and PLA dispersion.

Both the 1- and 2-step application methods result in more colorant uptake and improved color retention as compared to the 1-step method of Preparations 59 and 60 in which the hair was first treated with colorant solution followed by treatment with PLA dispersion.

Table 5, were trimmed and labeled. Each set of sample pairs was then placed in a small glass petri dish. In step 1 of this example, 2.5 mL of a mixture (as given in Color uptake was increased for any of the 1-step or 2-step procedures when 1.0% colorant is used as compared to 0.1% colorant. Dye retention was more difficult to assess visually.

The 2-step application method in which the hair is first treated with a PLA dispersion followed by treatment with colorant solution results in comparable uptake and comparable color retention following multiple shampooing as compared to the one-step (simultaneous) application of colorant and PLA dispersion.

Both the 1- and 2-step application methods result in more colorant uptake and improved color retention as compared to the 1-step method of Preparations 59 and 60 in which the hair was first treated with colorant solution followed by treatment with PLA dispersion.

Table 5) was then added into the dish, and a paintbrush was used to work the mixture evenly throughout the samples. Each sample set was picked up from the dish and combed through with several strokes before returning to dish. The dishes were then covered with aluminum foil. All samples were placed under a hooded hair dryer set to HI (32-37° C.) for 30 or 60 minutes. All samples were then rinsed with tap water and blown dry. Step 2 was then carried out similarly to the Step 1 procedure for Preparations 57-60 as given in Color uptake was increased for any of the 1-step or 2-step procedures when 1.0% colorant is used as compared to 0.1% colorant. Dye retention was more difficult to assess visually.

The 2-step application method in which the hair is first treated with a PLA dispersion followed by treatment with colorant solution results in comparable uptake and comparable color retention following multiple shampooing as compared to the one-step (simultaneous) application of colorant and PLA dispersion.

Both the 1- and 2-step application methods result in more colorant uptake and improved color retention as compared to the 1-step method of Preparations 59 and 60 in which the hair was first treated with colorant solution followed by treatment with PLA dispersion.

Table 5. Following the final heating period, samples were rinsed with tap water and blown dry. One sample from each pair was then shampooed with baby shampoo, rinsed and blown dry a total of five times.

Colorant uptake following the coloring procedure and colorant retention following washes was assessed visually. Color uptake was increased for any of the 1-step or 2-step procedures when 1.0% colorant is used as compared to 0.1% colorant. Dye retention was more difficult to assess visually.

The 2-step application method in which the hair is first treated with a PLA dispersion followed by treatment with colorant solution results in comparable uptake and comparable color retention following multiple shampooing as compared to the one-step (simultaneous) application of colorant and PLA dispersion.

Both the 1- and 2-step application methods result in more colorant uptake and improved color retention as compared to the 1-step method of Preparations 59 and 60 in which the hair was first treated with colorant solution followed by treatment with PLA dispersion.

TABLE 5

Coloring procedure for Preparations 53-60.
Mixture compositions A-E are given in Table 4.

| Preparation | Step 1 | | Step 2 | |
|---|---|---|---|---|
| Number | Mixture | Heat | Mixture | Heat |
| 53 | A | 30 min | (no Step 2) | |
| 54 | A | 60 min | (no Step 2) | |
| 55 | B | 30 min | (no Step 2) | |
| 56 | B | 60 min | (no Step 2) | |
| 57 | C | 30 min | D | 30 min |
| 58 | C | 30 min | E | 30 min |
| 59 | D | 30 min | C | 30 min |
| 60 | E | 30 min | C | 30 min |

Example 5

Acidic and Basic Dyes

Sixteen hair colorant compositions were prepared as given in Color compositions comprised of an acidic dye have increased color uptake and retention following shampoo washes when PLA is included. Color compositions comprised of a basic dye show little difference in color uptake and color retention when PLA is included.

Table 6 for formulations comprised of acid dyes, and in Table 7 for formulations comprised of basic dyes. All compositions were stirred until there were no visible solid dye particulates remaining and the resulting solution or dispersion appeared homogenous.

Two hair samples weighing approximately 500 mg each were prepared for each coloring composition. The two hair samples were placed on aluminum foil and then 1 mL of prepared coloring composition per two hair samples was pipetted onto the samples. Samples were then secured in aluminum foil packets and placed under the hooded hair dryer set on HI for 30 minutes. Samples were then removed from the foil packet, rinsed with warm tap water, and dried using a hand-held blow dryer set on warm heat and high speed. After drying, sample sets were washed using baby shampoo for up to 10 washes, with a final blow dry, similarly to the methods of Example 1.

Colorant uptake following the coloring procedure and colorant retention following washes was assessed visually. Color compositions comprised of an acidic dye have increased color uptake and retention following shampoo washes when PLA is included. Color compositions comprised of a basic dye show little difference in color uptake and color retention when PLA is included.

TABLE 6

Preparation numbers and coloring compositions comprised of mixtures of acid dye colorants. Balance of each composition is deionized water.

| | | wt % Colorant(s) | | | | | |
|---|---|---|---|---|---|---|---|
| Preparation Number | Colorant Mixture Name | Acid Black 1 | Acid Violet 43 | Acid Red 33 | Acid Orange 7 | Acid Yellow 23 | wt % LANDY PL-3000 |
| 61 | Gold | | | | 0.05 | 0.10 | — |
| 62 | Mahogany | | | 0.10 | 0.12 | | — |
| 63 | Burgundy | | 0.012 | 0.12 | | | — |
| 64 | Black Shine | 0.25 | 0.08 | | 0.20 | | — |
| 65 | Brown | 0.20 | 0.08 | | 0.25 | | — |
| 66 | Gold | | | | 0.05 | 0.10 | 20.0 |
| 67 | Mahogany | | | 0.10 | 0.12 | | 20.0 |
| 68 | Burgundy | | 0.012 | 0.12 | | | 20.0 |
| 69 | Black Shine | 0.25 | 0.08 | | 0.20 | | 20.0 |
| 70 | Brown | 0.20 | 0.08 | | 0.25 | | 20.0 |

TABLE 7

Preparation numbers and coloring compositions comprised of mixtures of basic dye colorants. Balance of each composition is deionized water.

| | | wt % Colorant(s) | | | | | |
|---|---|---|---|---|---|---|---|
| Preparation Number | Colorant Mixture Name | Basic Brown 17 | Basic Red 76 | Basic Blue 99 | Basic Yellow 57 | Basic Red 51 | wt % LANDY PL-3000 |
| 71 | Copper (Basic) | | | | 0.60 | 0.025 | — |
| 72 | Chestnut | 0.30 | 0.23 | 0.30 | 0.30 | | — |
| 73 | Purple | | | 0.35 | | 0.05 | — |
| 74 | Copper (Basic) | | | | 0.60 | 0.025 | 20.0 |
| 75 | Chestnut | 0.30 | 0.23 | 0.30 | 0.30 | | 20.0 |
| 76 | Purple | | | 0.35 | | 0.05 | 20.0 |

Example 6

Optical Density Measurents

Ten hair colorant compositions were prepared as shown in Tables 11-12 according to the methods of Example 1. For PLA compositions, LANDY PL-3000 was added to the solution after all dye and $CaCl_2$ was dissolved, and the mixture then stirred until a uniform dispersion was formed.

Three samples of bleached yellow-white hair, each approximately 4 in long and weighing 500 mg, were prepared for each colorant formulation. The coloring composition was then added to samples in an amount equal to 2 mL per hair sample and then worked into the samples using a dye brush. Samples were secured in aluminum foil and placed under a hooded hair dryer set to HI for 30 minutes. Samples were then removed from foil, rinsed with warm tap water, and dried using a hand-held blow dryer.

Optical densities in Black (B), cyan (C), magenta (M), and yellow (Y) were then determined with a Gretag Macbeth D19C densitometer using the extendable measuring head. Optical densities were determined at the crosswise center of each hair sample at 2 cm, 5 cm, and 9 cm from the lengthwise top of the hair sample, thus resulting in a total of nine densitometer measurements for each colorant formulation.

All samples were then shampooed with an herbal shampoo for a total of 10 washes, and were dried using a hand-held blow dryer following the final wash. Optical densities were then again determined using the same procedure and at the same positions as for the samples prior to washing.

The change in optical densities between an "initial" sample and the sample after coloring and rinsing and drying corresponds to the amount of dye uptake. For hair samples colored with compositions consisting of colorant and water only, the initial optical densities were determined from comparable optical density measurements taken of a bleached yellow-white hair sample.

LANDY PL-3000 coated on the hair shafts generally resulted in a slight whitening of the hair color. Therefore, for hair samples colored with compositions comprised of LANDY PL-3000, the initial optical densities were determined from comparable measurements taken of a bleached yellow-white hair sample that was treated with a 20% LANDY PL-3000 dispersion.

Initial optical densities for bleached yellow-blonde hair and LANDY PL-3000 treated hair are given in Table 8.

TABLE 8

Initial optical densities of bleached yellow-blonde and LANDY PL-3000 treated hair.

| Sample and channel | | Initial O.D. |
|---|---|---|
| Bleached yellow-blonde hair | B | 0.56 ± 0.04 |
| | C | 0.51 ± 0.03 |
| | M | 0.58 ± 0.04 |
| | Y | 0.74 ± 0.04 |

TABLE 8-continued

Initial optical densities of bleached yellow-blonde
and LANDY PL-3000 treated hair.

| Sample and channel | | Initial O.D. |
|---|---|---|
| LANDY PL-3000 treated hair | B | 0.51 ± 0.03 |
| | C | 0.47 ± 0.03 |
| | M | 0.52 ± 0.03 |
| | Y | 0.68 ± 0.03 |

Colorant formulations are given in Table 9 and Table 10. The results of the optical density measurements are summarized in Table 11 and selected optical density data are presented graphically in the FIGURE.

TABLE 9

Preparation number and colorant formulations comprised of mixtures of acid dye colorants. Balance of each composition is deionized water.

| | | wt % Colorant(s) | | | | | |
|---|---|---|---|---|---|---|---|
| Preparation Number | Mixture Name | Acid Black 1 | Acid Violet 43 | Acid Red 33 | Acid Orange 7 | wt % CaCl$_2$ | wt % LANDY PL-3000 |
| 77 | Burgundy | | 0.012 | 0.12 | | — | — |
| 78 | Black Shine | 0.25 | 0.08 | | 0.20 | — | — |
| 79 | Burgundy | | 0.012 | 0.12 | | 0.25 | 20.0 |
| 80 | Black Shine | 0.25 | 0.08 | | 0.20 | 0.25 | 20.0 |

TABLE 10

Preparation number and colorant formulations comprised of mixtures of basic dye colorants. Balance of each composition is deionized water.

| | | wt % Colorant(s) | | | | | | |
|---|---|---|---|---|---|---|---|---|
| Preparation Number | Mixture Name | Basic Brown 17 | Basic Red 76 | Basic Blue 99 | Basic Yellow 57 | Basic Red 51 | wt % CaCl$_2$ | wt % LANDY PL-3000 |
| 81 | Copper (basic) | | | | 0.60 | 0.025 | — | — |
| 82 | Chestnut | 0.30 | 0.23 | 0.30 | 0.30 | | — | — |
| 83 | Purple | | | 0.35 | | 0.05 | — | — |
| 84 | Copper (basic) | | | | 0.60 | 0.025 | 0.25 | 20.0 |
| 85 | Chestnut | 0.30 | 0.23 | 0.30 | 0.30 | | 0.25 | 20.0 |
| 86 | Purple | | | 0.35 | | 0.05 | 0.25 | 20.0 |

TABLE 11

Optical Density data for dye uptake and retention for Preparations 77-86.

| | | Colorant/CaCl$_2$/LANDY PL-3000/water | | Colorant/water ONLY | |
|---|---|---|---|---|---|
| | | Dye Uptake (change in O.D.) | Dye Retention (% Dye Taken Up) | Dye Uptake (change in O.D.) | Dye Retention (% Dye Taken Up) |
| Burgundy | B | 0.80 ± 0.08 | 90 ± 8% | 0.35 ± 0.08 | 69 ± 8% |
| | C | 0.40 ± 0.07 | 89 ± 7% | 0.29 ± 0.06 | 64 ± 7% |
| | M | 1.00 ± 0.11 | 94 ± 9% | 0.37 ± 0.09 | 70 ± 8% |
| | Y | 0.54 ± 0.08 | 87 ± 7% | 0.15 ± 0.08 | 27 ± 3% |
| Black Shine | B | 1.33 ± 0.18 | 90 ± 8% | 1.31 ± 0.10 | 80 ± 9% |
| | C | 1.49 ± 0.21 | 93 ± 9% | 1.38 ± 0.11 | 80 ± 10% |
| | M | 1.38 ± 0.20 | 94 ± 9% | 1.36 ± 0.12 | 81 ± 10% |
| | Y | 1.31 ± 0.17 | 94 ± 7% | 1.35 ± 0.11 | 82 ± 8% |

TABLE 11-continued

Optical Density data for dye uptake and retention for Preparations 77-86.

|  |  | Colorant/CaCl$_2$/ LANDY PL-3000/water | | Colorant/water ONLY | |
|---|---|---|---|---|---|
|  |  | Dye Uptake (change in O.D.) | Dye Retention (% Dye Taken Up) | Dye Uptake (change in O.D.) | Dye Retention (% Dye Taken Up) |
| Copper (basic) | B | 0.40 ± 0.07 | 89 ± 7% | 0.82 ± 0.17 | 85 ± 8% |
|  | C | 1.00 ± 0.11 | 94 ± 9% | 0.31 ± 0.10 | 75 ± 7% |
|  | M | 0.54 ± 0.08 | 87 ± 7% | 1.21 ± 0.28 | 89 ± 11% |
|  | Y | 0.68 ± 0.27 | 91 ± 24% | 1.32 ± 0.25 | 91 ± 10% |
| Chestnut | B | 1.57 ± 0.16 | 104 ± 13% | 1.64 ± 0.09 | 91 ± 6% |
|  | C | 1.83 ± 0.11 | 101 ± 9% | 1.71 ± 0.12 | 94 ± 8% |
|  | M | 1.31 ± 0.13 | 94 ± 9% | 1.81 ± 0.10 | 97 ± 7% |
|  | Y | 1.58 ± 0.21 | 98 ± 19% | 1.65 ± 0.07 | 98 ± 6% |
| Purple | B | 1.49 ± 0.21 | 93 ± 9% | 1.64 ± 0.19 | 91 ± 10% |
|  | C | 1.38 ± 0.20 | 94 ± 9% | 1.72 ± 0.25 | 94 ± 14% |
|  | M | 1.31 ± 0.17 | 94 ± 7% | 1.79 ± 0.21 | 98 ± 12% |
|  | Y | 1.38 ± 0.21 | 93 ± 17% | 1.29 ± 0.25 | 91 ± 13% |

For Burgundy colorant, comprised of acid dyes, the coloring composition comprised of LANDY PL-3000 increased dye uptake by more than a factor of two and improved dye retention by at least 20%, as measured in the Black, Cyan, and Magenta. The improvement in color uptake and retention as measured in Yellow upon addition of LANDY PL-3000 to the compositions was even greater than for B, C, and M channels.

In general for the other coloring compositions, the C, M, and Y channels paralleled the B channel in dye uptake and retention, that is, the B channel is a measure of spectrally-averaged dye uptake and retention. The dye retention and uptake in the B channel is therefore selected for presentation in Error! Reference source not found.1.

For Black Shine colorant, comprised of an acid dye, color uptake was comparable between the coloring compositions consisting of colorant and water only as compared to those comprised of LANDY PL-3000.

For Copper (basic) and Purple colorants, both comprised of basic dyes, color uptake was comparable between the coloring compositions consisting of colorant and water only as compared to those comprised of LANDY PL-3000. Color retention was slightly, but not significantly, greater for Copper (basic) and Purple colorants for compositions comprised of LANDY PL-3000.

For Chestnut colorant the coloring composition comprised of LANDY PL-3000 decreased color uptake slightly, and resulted in an insignificant decrease in dye retention on shampoo washes.

Example 7

Effect of Original Hair Color on the Coloring Process 26 hair colorant compositions were prepared as in Table 14 by mixing all components until all colorant and calcium chloride was completely dissolved and a homogeneous dispersion was formed. The coloring compositions were then used to color smooth straight medium blonde (SSMB), 25% gray, medium brown (MB), and wavy light red (WLR) hair types.

Three hair samples of each hair type were secured and placed onto aluminum foil, and then 1 mL of coloring composition was applied per hair sample and worked into the hair sample using a dye brush and comb. The hair samples were wrapped in aluminum foil and placed under a hooded hair dryer set to 'HI' for approximately 30 minutes. Samples were then removed from the hair dryer, rinsed with tap water, and then dried with a hand-held blow dryer. One sample was set aside and the remaining two samples were washed using herbal shampoo for a total of either 5 or 10 times.

Colorant uptake following the coloring procedure and colorant retention following washes was assessed visually. The colorant comprised of 20% LANDY PL-3000 results in improved color uptake on unbleached hair, particularly for the red shades evident in Mahogany, Purple, and Copper (acid) coloring compositions, as compared to colorants without the addition of LANDY PL-3000.

TABLE 12

Preparation numbers, hair types, and colorant formulations (aqueous).

| | | | wt % Colorant(s) | | | | | | | | |
|---|---|---|---|---|---|---|---|---|---|---|---|
| Preparation Number | Hair Type | Mixture Name | Acid Red 33 | Acid Orange 7 | Acid Black 1 | Acid Violet 43 | Acid Red 18 | Basic Blue 99 | Basic Red 51 | wt % CaCl$_2$ | wt % LANDY PL-3000 |
| 87 | SSMB | Mahogany | 0.10 | 0.12 | | | | | | 0.25 | — |
| 88 | 25% gray | | | | | | | | | | |
| 89 | MB | | | | | | | | | | |
| 90 | WLR | | | | | | | | | | |
| 91 | SSMB | Black Shine | | 0.20 | 0.25 | 0.08 | | | | 0.25 | — |
| 92 | 25% gray | | | | | | | | | | |
| 93 | MB | | | | | | | | | | |
| 94 | WLR | | | | | | | | | | |

TABLE 12-continued

Preparation numbers, hair types, and colorant formulations (aqueous).

| Preparation Number | Hair Type | Mixture Name | Acid Red 33 | Acid Orange 7 | Acid Black 1 | Acid Violet 43 | Acid Red 18 | Basic Blue 99 | Basic Red 51 | wt % CaCl$_2$ | wt % LANDY PL-3000 |
|---|---|---|---|---|---|---|---|---|---|---|---|
| 95 | SSMB | Purple | | | | | | 0.35 | 0.05 | 0.25 | |
| 96 | 25% gray | | | | | | | | | | |
| 97 | MB | | | | | | | | | | |
| 98 | WLR | | | | | | | | | | |
| 99 | MB | Copper (acid) | | 0.20 | | | 0.15 | | | 0.25 | |
| 100 | SSMB | Mahogany | 0.10 | 0.12 | | | | | | 0.25 | 20.0 |
| 101 | 25% gray | | | | | | | | | | |
| 102 | MB | | | | | | | | | | |
| 103 | WLR | | | | | | | | | | |
| 104 | SSMB | Black Shine | | 0.20 | 0.25 | 0.08 | | | | 0.25 | 20.0 |
| 105 | 25% gray | | | | | | | | | | |
| 106 | MB | | | | | | | | | | |
| 107 | WLR | | | | | | | | | | |
| 108 | SSMB | Purple | | | | | | 0.35 | 0.05 | 0.25 | |
| 109 | 25% gray | | | | | | | | | | |
| 110 | MB | | | | | | | | | | |
| 111 | WLR | | | | | | | | | | |
| 112 | MB | Copper (acid) | | 0.20 | | | 0.15 | | | 0.25 | 20.0 |

What is claimed is:

1. An aqueous colorant composition comprising poly (lactic acid) (PLA) and a colorant, wherein the PLA comprises 5.8-6.0 wt %. of the total colorant composition.

2. The composition of claim 1 wherein the PLA is an aqueous dispersion.

3. The composition of claim 1 wherein the colorant comprises a direct dye.

4. The composition of claim 1 wherein the colorant comprises a mixture of two or more direct dyes.

5. The composition of claim 1 further comprising a metal salt.

6. The composition of claim 1 further comprising a mineral additive.

7. The composition of claim 1 wherein the colorant that is whitener or tinting agent and comprises no more than 0.01% of the colorant composition.

8. A method of coloring hair comprising the steps of:
 a. First applying to the hair an aqueous PLA dispersion; and then
 b. subsequently applying a colorant to the hair.

* * * * *

UNITED STATES PATENT AND TRADEMARK OFFICE
CERTIFICATE OF CORRECTION

PATENT NO.            : 10,500,149 B2
APPLICATION NO.       : 14/984930
DATED                 : December 10, 2019
INVENTOR(S)           : Lago et al.

It is certified that error appears in the above-identified patent and that said Letters Patent is hereby corrected as shown below:

On the Title Page

Item (73) Assignees: "NATURAL COSMETICOS S.A." should read --NATURA COSMETICOS S.A.--.

Signed and Sealed this
Nineteenth Day of May, 2020

Andrei Iancu
*Director of the United States Patent and Trademark Office*